(12) United States Patent
Hyodo et al.

(10) Patent No.: US 10,390,878 B2
(45) Date of Patent: Aug. 27, 2019

(54) MEDICAL DEVICE AND MEDICAL SYSTEM

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 809 days.

(21) Appl. No.: 14/855,708

(22) Filed: Sep. 16, 2015

(65) Prior Publication Data

US 2016/0000503 A1    Jan. 7, 2016

Related U.S. Application Data

(63) Continuation of application No. PCT/JP2014/051230, filed on Jan. 22, 2014.
(Continued)

(51) Int. Cl.
*A61B 18/14* (2006.01)
*A61B 34/30* (2016.01)
*A61B 18/00* (2006.01)

(52) U.S. Cl.
CPC .......... *A61B 18/1492* (2013.01); *A61B 34/30* (2016.02); *A61B 18/1442* (2013.01);
(Continued)

(58) Field of Classification Search
CPC ............ A61B 18/1442; A61B 18/1492; A61B 2018/1422; A61B 2018/144; A61B 2018/1475
See application file for complete search history.

(56) References Cited

U.S. PATENT DOCUMENTS 2,541,246 A    2/1951    Held
5,443,475 A    8/1995    Auerbach et al.
(Continued)

FOREIGN PATENT DOCUMENTS

CN    202682047 U    1/2013
CN    1051011899 A    11/2015
(Continued)

OTHER PUBLICATIONS

International Search Report dated Mar. 4, 2014 issued in PCT/JP2014/051230.
(Continued)

*Primary Examiner* — Michael F Peffley
*Assistant Examiner* — Samantha M Good
(74) *Attorney, Agent, or Firm* — Scully, Scott, Murphy & Presser P.C.

(57) ABSTRACT

A medical device includes an insertion portion, and a driving mechanism coupled to the insertion portion, wherein the insertion portion includes a treatment portion configured to perform a treatment on a target portion, a joint portion capable of supporting the treatment portion and changing a direction of the treatment portion, a storage portion provided in the joint portion and capable of internally accommodating the treatment portion, and a driving force transmission portion connected to the joint portion and configured to transmit a driving force for changing the direction of the treatment portion to the joint portion, wherein the driving mechanism includes a driving force generation portion configured to generate the driving force, and wherein the treatment portion enters and exits the storage portion by the driving force transmitted from the driving force generation portion to the joint portion through the driving force transmission portion.

3 Claims, 15 Drawing Sheets

Related U.S. Application Data

(60) Provisional application No. 61/806,114, filed on Mar. 28, 2013.

(52) U.S. Cl.
CPC ............... *A61B 2018/00202* (2013.01); *A61B 2018/144* (2013.01); *A61B 2018/1422* (2013.01); *A61B 2018/1475* (2013.01); *A61B 2034/301* (2016.02); *A61B 2034/303* (2016.02)

(56) References Cited

U.S. PATENT DOCUMENTS

| | | | |
|---|---|---|---|
| 5,797,923 | A | 8/1998 | Aiyar et al. |
| 2006/0178657 | A1 | 8/2006 | Sugita et al. |
| 2007/0034211 | A1* | 2/2007 | Hug ............... A61B 18/042 128/876 |
| 2008/0312652 | A1 | 12/2008 | Bell et al. |
| 2010/0168787 | A1 | 7/2010 | Surti |
| 2011/0238053 | A1 | 9/2011 | Brannan et al. |

FOREIGN PATENT DOCUMENTS

| | | |
|---|---|---|
| JP | H11-169381 A | 6/1999 |
| JP | H11-332880 A | 12/1999 |
| JP | 2008-264253 A | 11/2008 |
| JP | 2011-200649 A | 10/2011 |
| JP | 2012-513871 A | 6/2012 |
| WO | 2010/078163 A1 | 7/2010 |
| WO | 2013/012018 A1 | 1/2013 |

OTHER PUBLICATIONS

Notice of Allowance dated Jul. 19, 2016 in related Japanese Patent Application No. 2015-508119.

Extended Supplementary European Search Report dated Nov. 8, 2016 in related European Patent Application No. 14 77 2887.7.

Chinese Office Action dated Dec. 2, 2016 in related Chinese Patent Application No. 201480017628.0.

\* cited by examiner

MEDICAL DEVICE AND MEDICAL SYSTEM

This application is a continuation application based on a PCT International Application No. PCT/JP2014/051230, filed on Jan. 22, 2014, whose priority is claimed on U.S. Provisional Application No. 61/806,114, filed on Mar. 28, 2013. The contents of the PCT International Application and the U.S. Provisional Application are incorporated herein by reference.

BACKGROUND OF THE INVENTION

Field of the Invention

The present invention relates to a medical device and a medical system.

Description of Related Art

When a conventional medical device having a needle-like, rod-like, or hook-like electrode or forceps or the like in a protruded state toward a distal end is inserted into a channel of a medical manipulator of an endoscope or the like, the conventional medical device may damage an inner surface of the channel or interfere with the inner surface of the channel to be prevented from smoothly passing through the channel. Thus, it is known that medical devices are provided with a cover-like member outside the electrode, the forceps, or the like or a mechanism for drawing the electrode, the forceps, or the like inside the cover-like member.

For example, a medical device provided with a storage portion to accommodate a treatment portion for the purpose of protecting an inner surface of a channel of an endoscope is disclosed in Japanese Unexamined Patent Application, First Publication No. 2008-264253.

SUMMARY OF THE INVENTION

According to a first aspect of the present invention, a medical device includes: an insertion portion which is capable of being inserted into a body; and a driving mechanism which is coupled to the insertion portion, wherein the insertion portion has a treatment portion which is configured to perform a treatment on a treatment target portion; a joint portion which is configured to be capable of supporting the treatment portion and changing a direction of the treatment portion; a storage portion which is configured in the joint portion and capable of internally accommodating the treatment portion; and a driving force transmission portion which is connected to the joint portion and configured to transmit a driving force for changing the direction of the treatment portion to the joint portion, wherein the driving mechanism includes a driving force generation portion which is configured to generate the driving force connected to the driving force transmission portion, and wherein the treatment portion enters and exits the storage portion by the driving force transmitted from the driving force generation portion to the joint portion through the driving force transmission portion.

According to a second aspect of the present invention, in the medical device according to the first aspect, the treatment portion may include an incision electrode which is configured to receive supply of a high-frequency current to incise living tissue, the joint portion may include a switching mechanism which is configured to switch a conductive state of the high-frequency current for the incision electrode, the insertion portion may include a power supplying cable which is connected to the switching mechanism and from which the high-frequency current is applied, the driving mechanism may include a plug which is connected to the power supplying cable and connectable to a high-frequency power supply device, and the switching mechanism may cut off a current applied to the power supplying cable and the incision electrode when the incision electrode is positioned inside the storage portion, and may electrically connect the power supplying cable and the incision electrode when the incision electrode is positioned outside the storage portion.

According to a third aspect of the present invention, the medical device according to the first or second aspect may further include a cleaning mechanism in which the treatment portion removes a foreign substance attached to the treatment portion in a process of movement from an outside of the storage portion to an inside of the storage portion or within the storage portion.

According to a fourth aspect of the present invention, a medical system may include the medical device according to any one of the first to third aspects; a master medical manipulator configured to receive an operation input from an operator; a control unit connected to the master medical manipulator; a slave medical manipulator connected to the control unit and connected to the driving mechanism; and a determination unit provided in the control unit and configured to determine a state in which the treatment portion is inside the storage portion and a state in which the treatment portion is outside the storage portion.

DETAILED DESCRIPTION OF THE INVENTION

First Embodiment

An embodiment of the medical device of the present invention will be described with reference to FIGS. 1 to 6.

Figure 1:
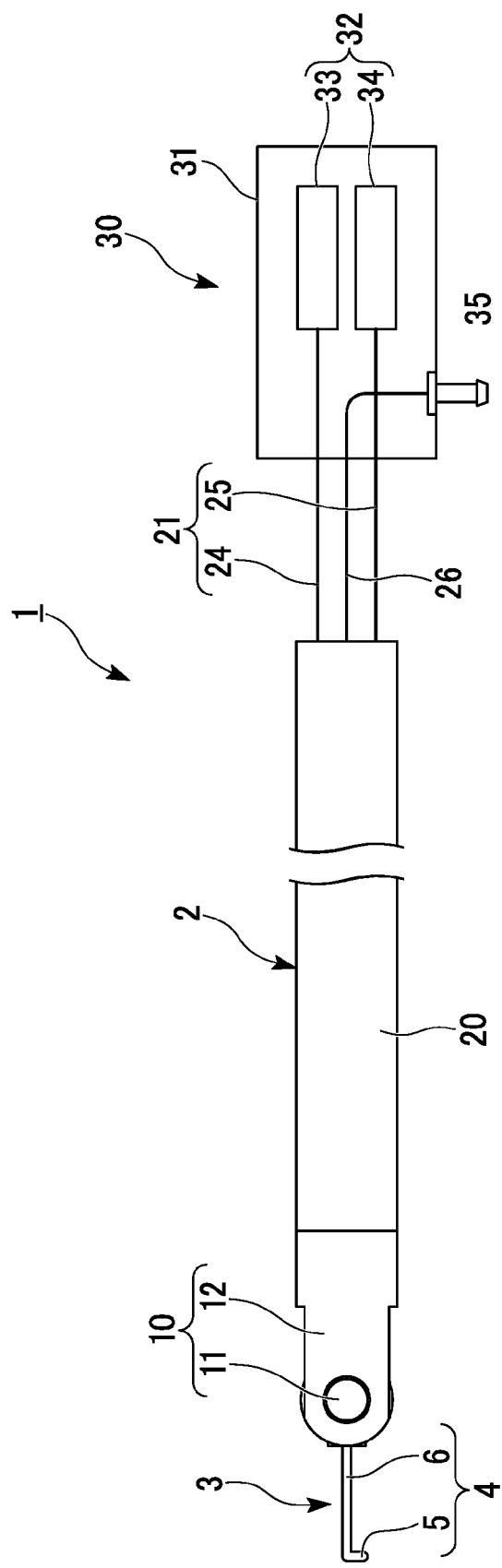
FIG. 1 is a schematic view showing a medical device of a first embodiment of the present invention.
Figure 2:
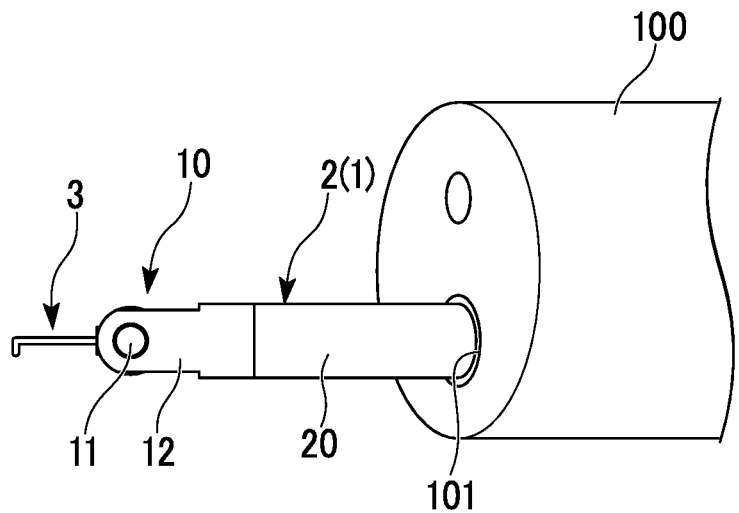
FIG. 2 is a schematic view showing a state in which the medical device is attached to an endoscope.
Figure 3:
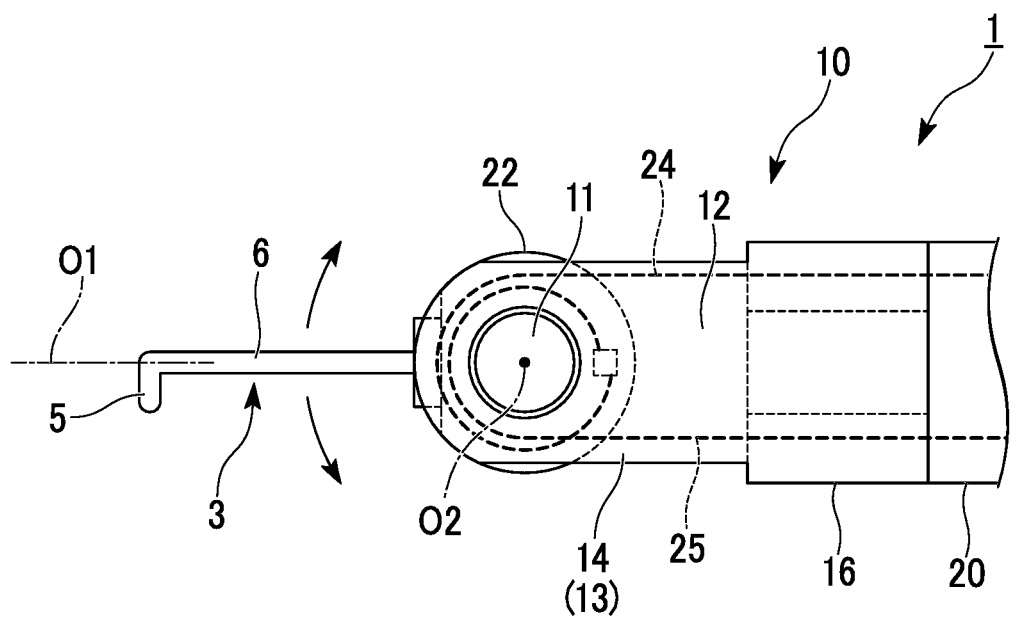
FIG. 3 is a schematic view showing an enlarged distal end part of the medical device in a plan view of the medical device.
Figure 4:
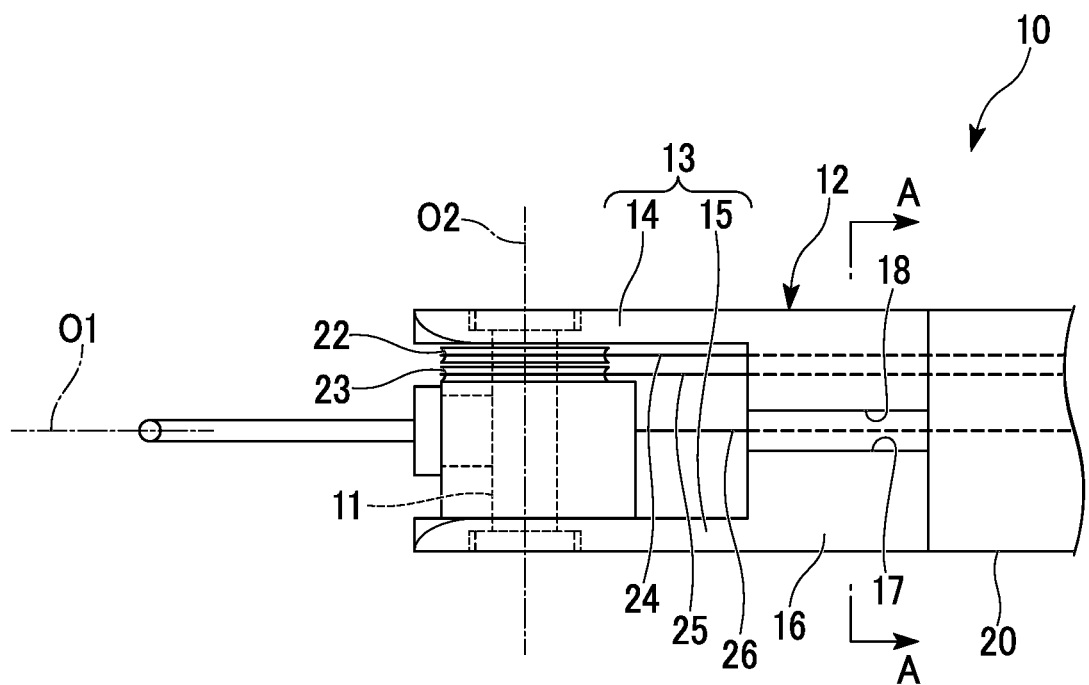
FIG. 4 is a schematic view showing an enlarged distal end part of the medical device in a side view of the medical device.
Figure 5:
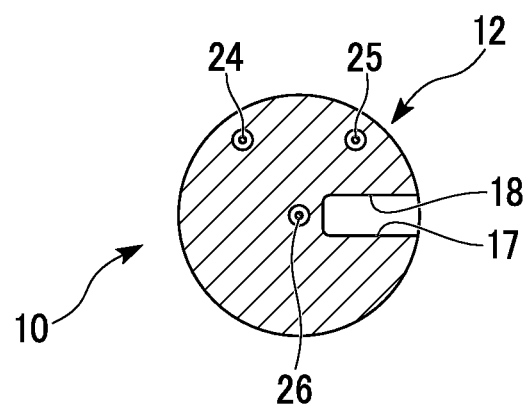
FIG. 5 is a cross-sectional view taken along line A-A of FIG. 4.
Figure 6:
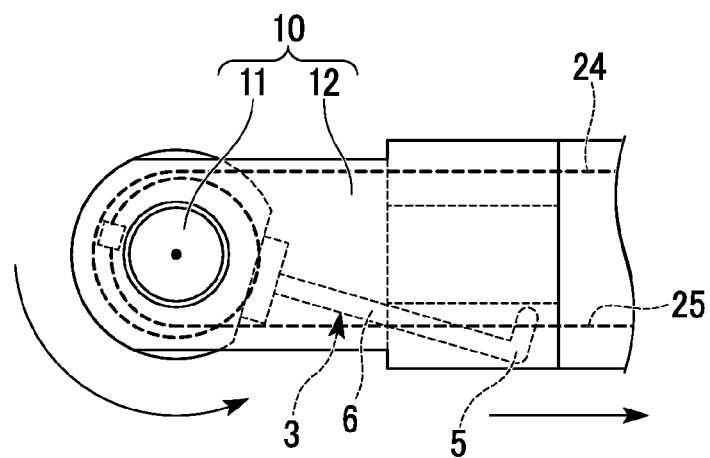
FIG. 6 is a schematic view showing an enlarged distal end part of the medical device in a plan view of the medical device.

FIG. 1 is a schematic view showing a medical device of the first embodiment of the present invention. FIG. 2 is a schematic view showing a state in which the medical device is attached to an endoscope. FIG. 3 is a schematic view showing an enlarged distal end part of the medical device in a plan view of the medical device. FIG. 4 is a schematic view showing an enlarged distal end part of the medical device in a side view of the medical device. FIG. 5 is a cross-sectional view taken along line A-A of FIG. 4. FIG. 6 is a schematic view showing an enlarged distal end part of the medical device in a plan view of the medical device.

As shown in FIG. 1, the medical device 1 includes an insertion portion 2 capable of being inserted into a body and a driving mechanism 30 coupled to the insertion portion 2.

The insertion portion 2 has an elongated shape capable of being inserted into the inside of a forceps channel 101 or the like in the endoscope 100 (see FIG. 2) and other well-known medical manipulators. As shown in FIG. 1, the insertion portion 2 includes a treatment portion 3, a joint portion 10, a flexible tube portion 20, a driving force transmission portion 21, and a power supplying cable 26. Hereinafter, in the present specification, an end on which the treatment portion 3 of the insertion portion 2 is provided is referred to as a distal end and an end opposing the end on which the treatment portion 3 is provided is referred to as a proximal end.

The treatment portion 3 performs a treatment on a treatment target portion. The treatment portion 3 of this embodiment has an incision electrode 4 configured to receive a supply of a high-frequency current to incise living tissue.

The incision electrode 4 has a rod-like shaft portion 6 and a hook portion 5 provided at a distal end of the shaft portion 6. The shaft portion 6 and the hook portion 5 include a metal wire having conductivity. The metal wire serving as the incision electrode 4 has a bent shape at a boundary part between the shaft portion 6 and the hook portion 5. In the shaft portion 6, an insulation film with which an outer surface of the metal wire is covered may be provided. The hook portion 5 of the incision electrode 4, for example, may be round. The incision electrode 4 may be configured without the hook portion 5.

As shown in FIGS. 3 and 4, the joint portion 10 has a rotating shaft 11 to which a proximal end of the shaft portion 6 of the incision electrode 4 is fixed and a support portion 12 configured to support the rotating shaft 11.

The rotating shaft 11 has an approximate columnar shape, and a centerline O1 of the shaft portion 6 and a centerline O2 of the rotating shaft 11 are perpendicular to each other. The rotating shaft 11 is coupled to the support portion 12 so that the rotating shaft 11 is rotatable with respect to the support portion 12 using the centerline O2 as a center of rotation.

The support portion 12 includes a coupling portion 13 coupled to the rotating shaft 11, a fixing portion 16 fixed to the flexible tube portion 20, and a storage portion 18 disposed between the coupling portion 13 and the fixing portion 16.

The coupling portion 13 supports both ends of the rotating shaft 11 with a predetermined clearance so that the rotating shaft 11 is freely rotatable about a centerline which is a center of rotation. In this embodiment, the coupling portion 13 has a first wall portion 14 to which a first end of the rotating shaft 11 is connected in a centerline direction of the rotating shaft 11 and a second wall portion 15 to which a second end of the rotating shaft 11 is connected in the centerline direction of the rotating shaft 11. The coupling portion 13 defines the direction of the rotation center of the rotating shaft 11.

The fixing portion 16 is a portion configured to fix the coupling portion 13 to a distal end of the flexible tube portion 20. The above-described power supplying cable 26 and a first wire 24 and a second wire 25 constituting the driving force transmission portion 21 are inserted into the inside of the fixing portion 16. Further, a part of an outer circumference surface of the fixing portion 16 has a long slit 17 in a linear direction in which a distal end and a proximal end are connected. The slit 17 formed in the fixing portion 16 is an entrance at the time of storing the treatment portion 3 within the storage portion 18.

As shown in FIGS. 4 and 5, the storage portion 18 is provided in the support portion 12. A shape of the storage portion 18 is defined according to an inner side surface of the coupling portion 13 and an inner surface of the fixing portion 16. The storage portion 18 can accommodate at least part of the incision electrode 4 which is the treatment portion 3 (see FIG. 6). The storage portion 18 may accommodate the entire incision electrode 4.

The joint portion 10 can support the treatment portion 3 or change the direction of the treatment portion 3. Further, it is possible to accommodate the treatment portion 3 within the storage portion 18 or remove the treatment portion 3 from within the storage portion 18.

The flexible tube portion 20 shown in FIG. 1 is a flexible tubular member into which the first wire 24, the second wire 25, and the power supplying cable 26 are internally inserted. The first wire 24 and the second wire 25 constitute the driving force transmission portion 21.

As shown in FIG. 4, the driving force transmission portion 21 has a first pulley 22 and a second pulley 23, the first wire 24, and the second wire 25 having the end portion of the distal end fixed to the second pulley 23. Each of the first pulley 22 and the second pulley 23 is formed in a disk shape and has a center on the rotation center of the rotating shaft 11. The first wire 24 has an end portion of a distal end side fixed to the first pulley 22. The second wire 25 has an end portion of a distal end side fixed to the second pulley 23. Both the first pulley 22 and the second pulley 23 are fixed to the rotating shaft 11. Thus, the first pulley 22 and the second pulley 23 rotates integrally with the rotating shaft 11. Instead of fixing the first pulley 22 and the second pulley 23 to the rotating shaft 11, the end portion of the distal end of the first wire 24 and the end portion of the distal end of the second wire 25 may be directly fixed to the rotating shaft 11 since the first pulley 22 and the second pulley 23 may not be included.

A direction in which the first wire 24 is wound around the first pulley 22 and a direction in which the second wire 25 is wound around the second pulley 23 are opposed to each other (see FIG. 3). A length in a circumferential direction in which the first wire 24 is wound around the first pulley 22 and a length in a circumferential direction in which the second wire 25 is wound around the second pulley define a movable range of the treatment portion 3 when the treatment portion 3 is used. As the movable range of the treatment portion 3 of this embodiment, a movable range of an extent to which the treatment portion 3 can be positioned within the storage portion 18 and the treatment portion 3 can be exposed from the storage portion 18 is minimally necessary. At least to satisfy the movable range, the first wire 24 is wound on the first pulley 22 and the second wire 25 is wound on the second pulley 23.

As the first wire 24 and the second wire 25, a wire including known materials such as stainless steel and a resin may be appropriately selected and adopted. The first wire 24 and the second wire 25 may be made of the same material or made of different materials.

As shown in FIG. 1, the proximal end of the first wire 24 and the proximal end of the second wire 25 are drawn into the driving mechanism 30 through the inside of the flexible tube portion 20 of the insertion portion 2. Therefore, the proximal end of the first wire 24 and the proximal end of the second wire 25 are connected to a driving force generation portion 32. The driving force generation portion 32 generates a driving force for moving the first wire 24 and the second wire 25 in their centerline directions (a longitudinal axis direction of the insertion portion 2). The driving force generated by the driving force generation portion 32 is transmitted to the joint portion 10 as a driving force for changing the direction of the treatment portion 3 through the first wire 24, the second wire 25, the first pulley 22, and the second pulley 23 of the driving force transmission portion 21.

As shown in FIGS. 1 and 4, the power supplying cable 26 is a flexible wire. The power supplying cable 26 has a conductive core wire through which a high-frequency current flows and an insulation film with which the core wire is covered. A distal end of the power supplying cable 26 is electrically connected to a metal wire of the incision electrode 4. The proximal end of the power supplying cable 26 is fixed to a plug 35, to be described below, disposed in the driving mechanism 30. Thereby, according to the medical device 1 of this embodiment, it is possible to supply the high-frequency current from the plug 35 to the incision electrode 4 through the power supplying cable 26.

As shown in FIG. 1, the driving mechanism 30 includes a base 31, the driving force generation portion 32, and the plug 35.

The driving force generation portion 32 has a first actuator 33 and a second actuator 34. The first actuator 33 is configured to generate a driving force for pulling the first wire 24. The second actuator 34 is configured to generate a driving force for pulling the second wire 25. Specific configurations of the first actuator 33 and the second actuator 34 are not limited as long as an appropriate pulling force can be transmitted to the first wire 24 and the second wire 25. For example, in the first actuator 33 and the second actuator 34, a mechanism of converting the driving force of a motor into linear movement using a rack-and-pinion and pulling the first wire 24 and the second wire 25 may be used. As another example, in the first actuator 33 and the second actuator 34, a mechanism which has pulleys on which the first wire 24 and the second wire 25 are wound and rotates the pulleys using motors may be used.

The plug 35 includes a conductor connectable to a well-known high-frequency power supply device and is connected to a proximal end of the power supplying cable 26.

Next, an operation of the medical device 1 of this embodiment will be described.

The medical device 1, for example, is inserted into the channel 101 in a medical manipulator such as an endoscope 100 shown in FIG. 2. The channel 101 is provided to guide a forceps or another device to a treatment target portion. At the time of insertion into the channel 101, one (the second wire 25 in this embodiment) of the first wire 24 and the second wire 25 is pulled by the driving force generation portion 32 so that the treatment portion 3 enters the storage portion 18. In this embodiment, the second actuator 34 of the driving force generation portion 32 pulls the second wire 25 toward the proximal end and the driving force of the first actuator 33 is released, so that the first wire 24 is freely advanced and retracted in the centerline direction (the longitudinal axis direction of the insertion portion 2). Thereby, the incision electrode 4 which is the treatment portion 3 is accommodated within the storage portion 18 (see FIG. 6). In a state in which the treatment portion 3 is accommodated within the storage portion 18, the length of the treatment portion 3 is shorter in the linear direction in which the distal end and the proximal end are connected as compared with that in a state in which the treatment portion 3 is outside the storage portion 18 (see FIGS. 3 and 6). Thus, when the channel 101 is in a curved state, the treatment portion 3 is less likely to interfere with an inner surface of the channel or the treatment portion 3 is less likely to damage the inner surface of the channel 101.

In a state in which the treatment portion 3 is accommodated within the storage portion 18, the treatment portion 3 is guided to the vicinity of the treatment target portion. In a state in which the treatment portion 3 and the joint portion 10 are drawn out from the distal end of the channel 101, the treatment portion 3 is moved from the inside to the outside of the storage portion 18 when a treatment using the treatment portion 3 is performed on the treatment target portion. In order to move the treatment portion 3 from the inside to the outside of the storage portion 18, the first wire 24 is pulled toward the proximal end using the first actuator 33 and the driving force of the second actuator 34 is released in this embodiment. Thereby, the first pulley 22 and the second pulley 23 and the rotating shaft 11 fixed thereto rotate so that the treatment portion 3 exits the storage portion 18 through the slit 17 of the storage portion 18. As a result, the incision electrode 4 of the treatment portion 3 rotates around the center of rotation O2 of the rotating shaft 11 and therefore moves from the inside of the storage portion 18 to the outside of the storage portion 18 so that a desired direction and orientation suitable for the treatment are provided.

In this embodiment, the high-frequency current is supplied to the incision electrode 4 which is the treatment portion 3 through the power supplying cable 26, thereby incising the treatment target tissue. At this time, it is possible to optimize the direction or orientation of the incision electrode 4 by performing an appropriate pulling operation on the first wire 24 and the second wire 25.

In addition, when the incision treatment on the treatment target tissue ends or it is necessary to replace the medical device 1, it is possible to remove the medical device 1 from the channel 101 without the contact of the treatment portion 3 with the inner surface of the channel 101 by pulling the second wire 25 toward the proximal end and storing the treatment portion 3 within the storage portion 18 again.

According to the medical device 1 of this embodiment, it is possible to accommodate the treatment portion 3 within the joint portion 10 by rotating the treatment portion 3 around the center of rotation of the rotating shaft 11. Thus, it can be used as both a mechanism for optimizing a direction or an orientation of the treatment portion 3 when a treatment on a treatment target portion is performed using the treatment portion 3 and a mechanism for moving the treatment portion 3 to accommodate the treatment portion 3 in the storage portion 18. Thereby, it is possible to reduce the size of the medical device 1 as compared with when a configuration dedicated to accommodate the treatment portion 3 is separately provided.

In addition, because the treatment portion 3 is accommodated inside the coupling portion 13 and the fixing portion 16 in the joint portion 10, it is possible to fit a treatment tool within a range of a rigid length produced by the coupling portion 13 and the fixing portion 16 when the treatment portion 3 is in an accommodated state. Thereby, it is possible to easily pass the insertion portion 2 of the medical device 1 within the channel 101 in the curved state.

Second Embodiment

Next, another embodiment of the medical device 1 of the present invention will be described with reference to FIGS. 7 to 12. In this embodiment and subsequent embodiments, the same reference signs are assigned to similar components to those disclosed in the above-described embodiment and redundant description thereof will be omitted.

Figure 7:
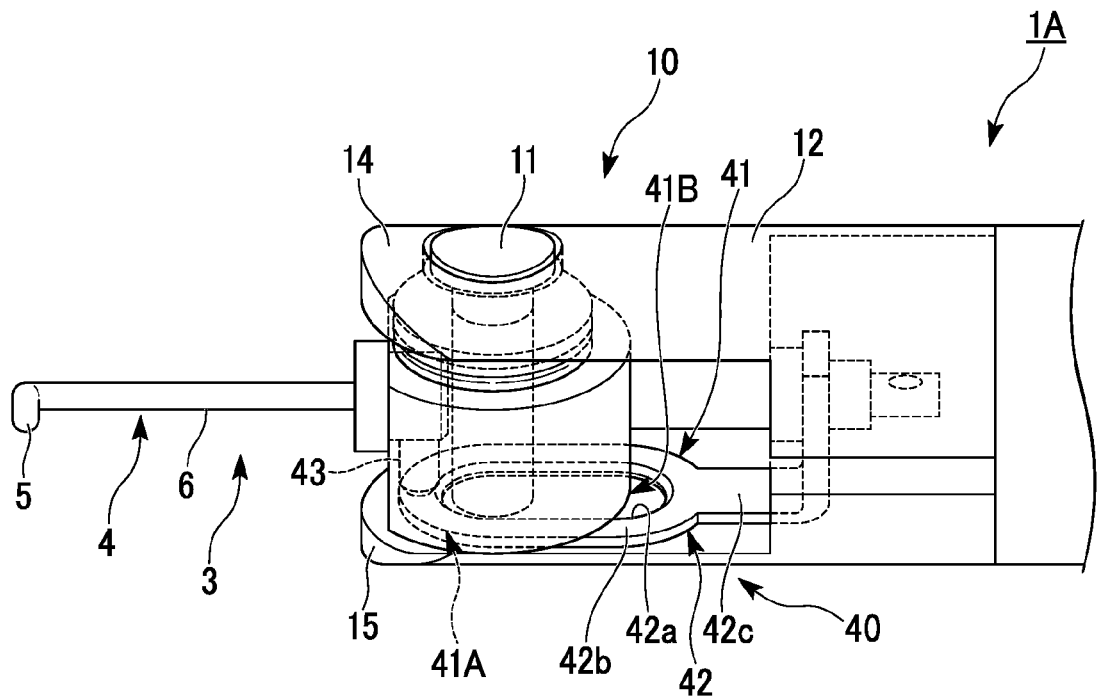
FIG. 7 is a schematic perspective view showing an enlarged distal end part of a medical device of a second embodiment of the present invention.
Figure 8:
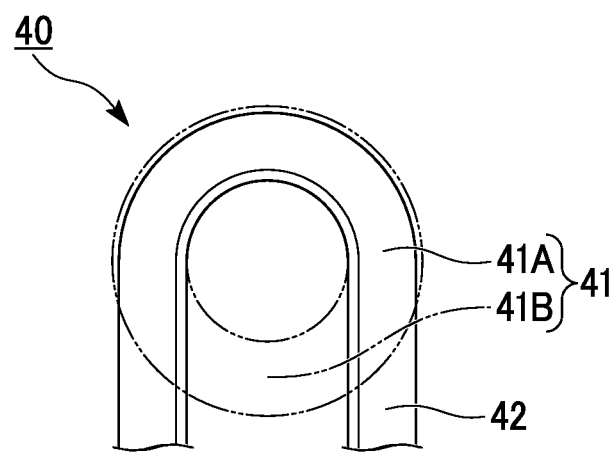
FIG. 8 is a schematic plan view showing a configuration of part of a switching mechanism provided at the distal end part of the medical device.
Figure 9:
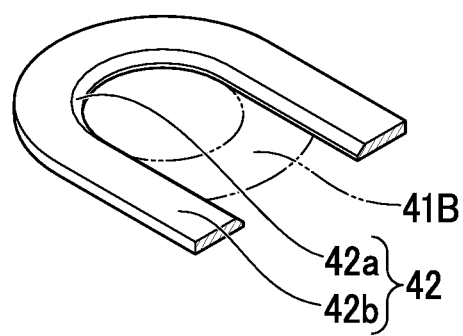
FIG. 9 is a schematic perspective view showing a partial cross section showing a shape of a spring terminal in the switching mechanism provided at the distal end part of the medical device.
Figure 10:
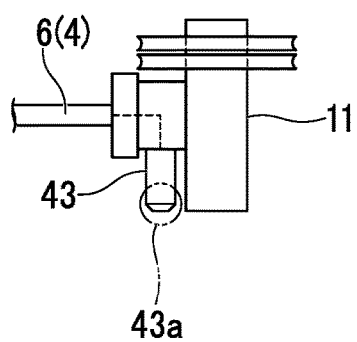
FIG. 10 is a schematic side view showing a configuration of a columnar terminal in the switching mechanism provided at the distal end part of the medical device.
Figure 11:
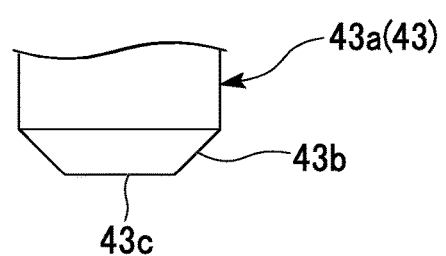
FIG. 11 is a partially enlarged view of FIG. 10.
Figure 12:
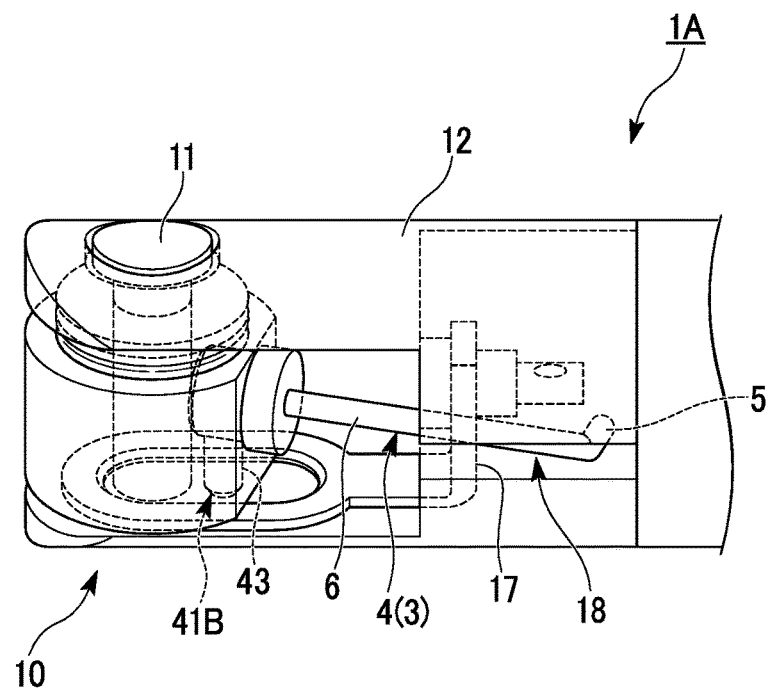
FIG. 12 is a schematic perspective view showing an operation of the medical device.

FIG. 7 is a schematic perspective view showing an enlarged distal end part of a medical device of the second embodiment of the present invention. FIG. 8 is a schematic plan view showing a configuration of part of a switching mechanism provided at the distal end part of the medical device. FIG. 9 is a schematic perspective view showing a partial cross section showing a shape of a spring terminal in the switching mechanism provided at the distal end part of the medical device. FIG. 10 is a schematic side view showing a configuration of a columnar terminal in the switching mechanism provided at the distal end part of the medical device. FIG. 11 is a partially enlarged view of FIG. 10. FIG. 12 is a schematic perspective view showing an operation of the medical device.

As shown in FIG. 7, the medical device 1A of this embodiment has a different configuration from that of the medical device 1 in the above-described first embodiment. In the present embodiment, the medical device 1A has a mechanism for releasing an electrical connection between the incision electrode 4 and the power supplying cable 26 at a storage time. That is, the medical device 1A of this embodiment further includes a switching mechanism 40 in a joint portion 10.

The switching mechanism 40 has a curved contact portion 41 provided in any one (a second wall portion 15 in this embodiment) of a first wall portion 14 and the second wall portion 15 and a columnar terminal 43 electrically connected to a metal wire of an incision electrode 4.

As shown in FIGS. 7 and 8, the curved contact portion 41 is an annular portion having a conductive region 41A configured to form part of an arc and an insulation region 41B configured to form part of an arc having the same radius as the conductive region 41A and provided to be adjacent to the conductive region 41A.

In the conductive region 41A, a spring terminal 42 for applying a high-frequency current to the incision electrode 4 is disposed. The spring terminal 42 has a biasing force for pressing the spring terminal 42 to the columnar terminal 43 and is an arc-like plate spring having approximately the same radius as the arc of the conductive region 41A.

As shown in FIG. 9, a sloped portion 42a is formed in a boundary part between the conductive region 41A and the insulation region 41B in the spring terminal 42. The sloped portion 42a is used for reducing a step difference of the insulation region 41B and the spring terminal 42. In addition, a surface directed toward the columnar terminal 43 in a part except the sloped portion 42a from a part positioned within the conductive region 41A of the spring terminal 42 is a flat portion 42b. The flat portion 42b can be in contact with a protruding end of the columnar terminal 43. Further, as shown in FIG. 7, a lead portion 42c is provided on a proximal end of the spring terminal 42 and electrically connects the spring terminal 42 and the power supplying cable 26.

The insulation region 41B is a region insulated from the power supplying cable 26. When the columnar terminal 43 is disposed in the insulation region 41B, the columnar terminal 43 is configured to prevent the supply of a high-frequency current from being received from the power supplying cable 26 (see FIG. 12). Although the columnar terminal 43 is configured to prevent physical contact with the spring terminal 42 in the insulation region in this embodiment, the insulation region 41B may have an insulator or may partially have a conductor as long as the insulation region 41B is insulated from the power supplying cable 26.

As shown in FIGS. 10 and 11, the columnar terminal 43 is a columnar conductor integrated with a metal wire of the incision electrode 4 or fixed to the metal wire. The columnar terminal 43 is provided to protrude from an outer surface of the shaft portion 6 toward the outside in a radial direction of the shaft portion 6. A protruding end portion 43a of the columnar terminal 43 is contactable with the flat portion 42b of the spring terminal 42 and the insulation region 41B. That is, the protruding end portion 43a of the columnar terminal 43 performs a turning motion around the center of rotation integrally with the rotating shaft 11 when the rotating shaft 11 rotates around the center of rotation of the rotating shaft 11. The turning radius of the protruding end portion 43a of the columnar terminal 43 is approximately equal to the radius of the curved contact portion 41.

In a boundary part between the insulation region 41B and the conductive region 41A of the curved contact portion 41, a step between the insulation region 41B and the spring terminal 42 is formed. As shown in FIG. 11, a tapered portion 43b is formed at a peripheral portion of the protruding end portion 43a of the columnar terminal 43 to easily overcome the step between the insulation region 41B and the spring terminal 42. Therefore, in an outer surface of the protruding end portion 43a of the columnar terminal 43, an inside region of the tapered portion 43b is a flat portion 43c contactable with the surface of the flat portion 42b of the spring terminal 42.

Next, an operation of the switching mechanism 40 will be mainly described with respect to an operation of the medical device 1A of this embodiment.

As shown in FIG. 12, the protruding end portion 43a of the columnar terminal 43 is positioned in the insulation region 41B when the incision electrode 4 is positioned within the storage portion 18. Therefore, the switching mechanism 40 cuts off a current applied to the power supplying cable 26 and the incision electrode 4. In addition, as shown in FIG. 7, the protruding end portion 43a of the columnar terminal 43 is in contact with the flat portion 42b of the spring contact point with respect to the conductive region 41A when the incision electrode 4 is positioned outside the storage portion 18. Therefore, the switching mechanism 40 electrically connects the power supplying cable 26 and the incision electrode 4.

According to the medical device 1A of this embodiment, no high-frequency current is applied to the incision electrode 4 when the incision electrode 4 which is the treatment portion 3 is accommodated within the storage portion 18. Thus, even when an operation of erroneously applying a high-frequency current is performed when the incision electrode 4 is accommodated, no high-frequency current flows through the incision electrode 4. Therefore, the medical device 1A according to the present embodiment is hard to be damaged and is very safe as compared with the medical device 1 according to the first embodiment.

Third Embodiment

Next, a third embodiment of the medical device 1 of the present invention will be described with reference to FIGS. 13 to 15.

Figure 13:
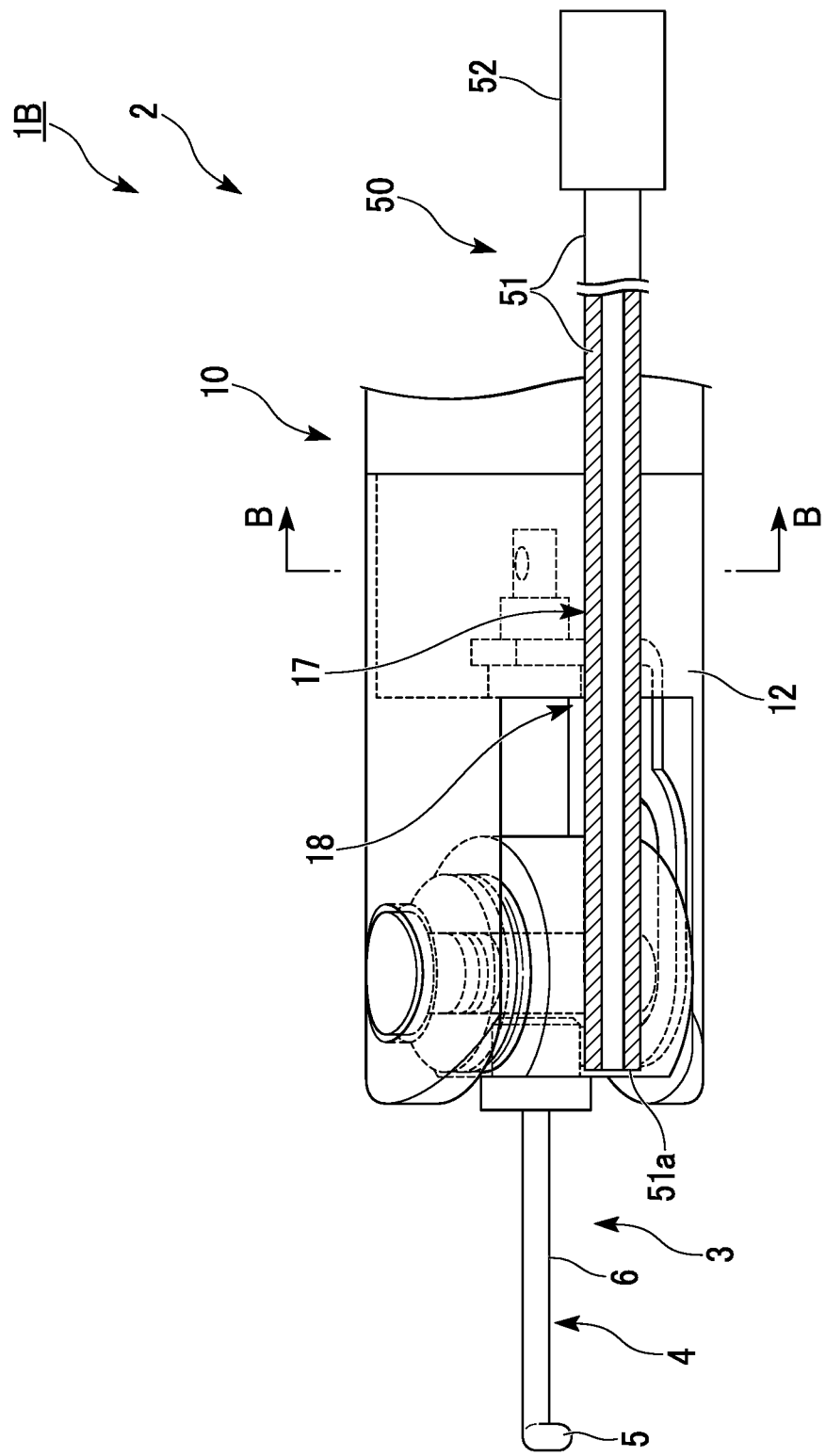
FIG. 13 is a schematic perspective view showing a medical device of a third embodiment of the present invention in a partial cross section.
Figure 14:
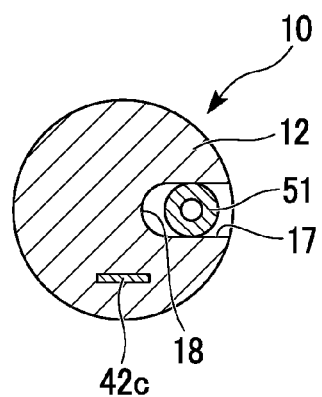
FIG. 14 is a cross-sectional view taken along line B-B of FIG. 13.

FIG. 13 is a schematic perspective view showing a medical device of a third embodiment of the present invention in a partial cross section. FIG. 14 is a cross-sectional view taken along line B-B of FIG. 13. FIG. 15 is a schematic perspective view showing a partial cross section showing an operation of the medical device. FIG. 16 is a schematic perspective view showing a configuration of a modified example of the medical device.

As shown in FIG. 13, the medical device 1B of this embodiment has a different configuration from the medical device 1 of the above-described first embodiment in that the medical device 1B has a mechanism for cleaning the incision electrode 4 during a storage operation. That is, the medical device 1B of this embodiment further includes a cleaning mechanism 50 in a joint portion 10.

As shown in FIG. 13, the cleaning mechanism 50 has a flexible water supply tube 51 through which cleaning water flows and a position change mechanism 52 configured to change a position of an ejection port 51a of the water supply tube 51.

Figure 15:
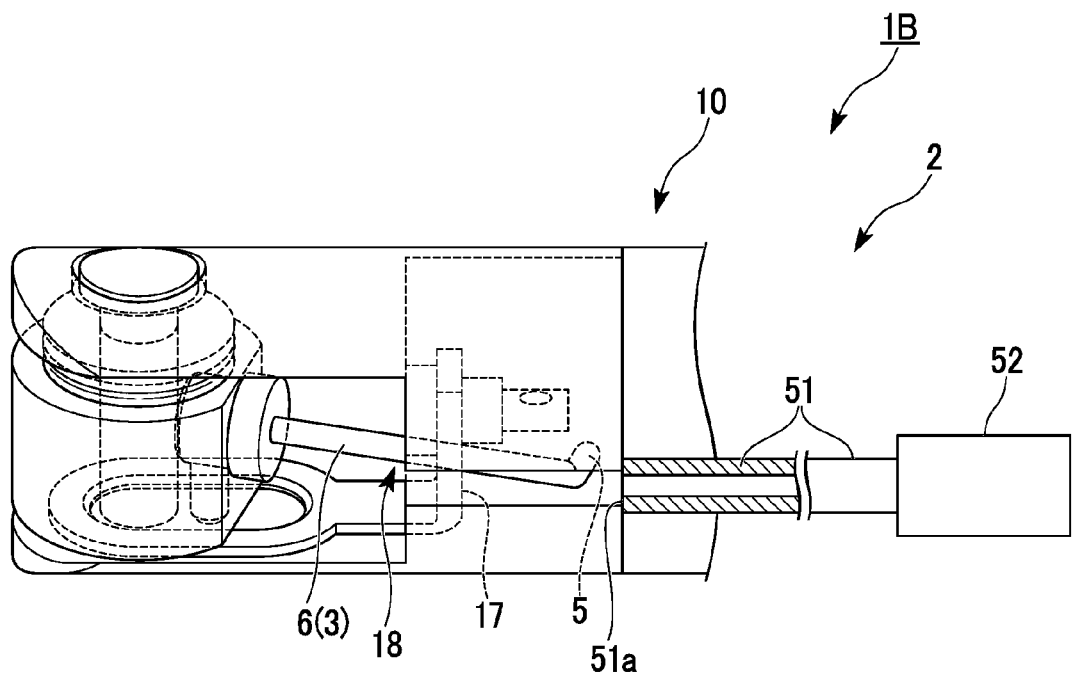
FIG. 15 is a schematic perspective view showing a partial cross section showing an operation of the medical device.
Figure 16:
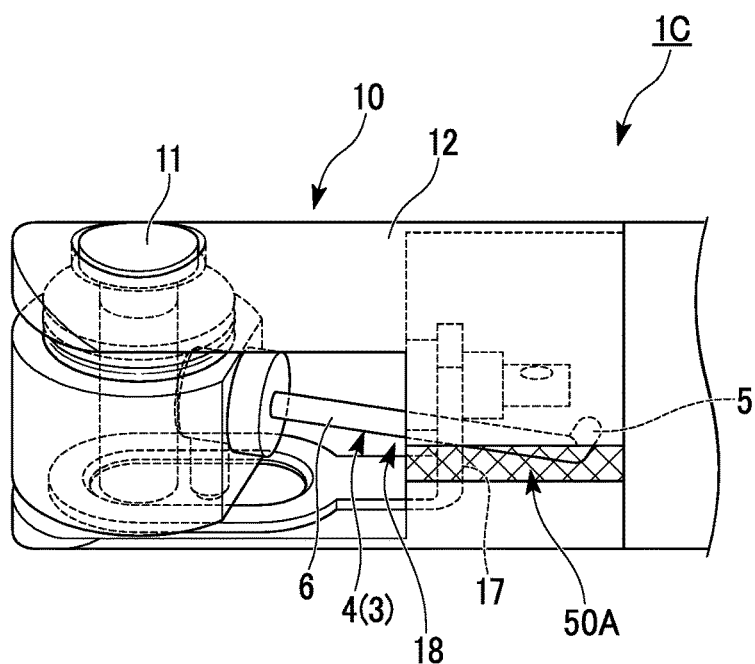
FIG. 16 is a schematic perspective view showing a configuration of a modified example of the medical device.

As shown in FIGS. 13 and 15, the water supply tube 51 is a tube disposed along a longitudinal axis of an insertion portion 2. For example, the water supply tube 51 is disposed within a flexible tube portion 20 (see FIG. 1) through a gap of the slit 17 and extends to the driving mechanism 30. An opening of a distal end of the water supply tube 51 is the ejection port 51a of the cleaning water and an opening of a proximal end of the water supply tube 51 is a supply port of the cleaning water. The water supply tube 51 is freely advanced and retracted to and from the insertion portion 2 in a longitudinal direction of the insertion portion 2. The advance and retraction motions of the water supply tube 51 in the longitudinal direction of the insertion portion 2 are controlled by the position change mechanism 52.

The position change mechanism 52 is disposed in the driving mechanism 30 and coupled to a part positioned within the driving mechanism 30 of the water supply tube 51. The position change mechanism 52 has an actuator (not shown) configured to advance and retract the water supply tube 51 along the centerline thereof (a longitudinal axis direction of the insertion portion 2), etc. When the position change mechanism 52 moves the water supply tube 51 to a most distal end, the ejection port 51a is positioned at the distal end of the joint portion 10. When the position change mechanism 52 moves the water supply tube 51 to the most proximal end, the ejection port 51a is positioned at a proximal end of the slit 17.

The position change mechanism 52 may not be provided in the medical device 1B. In this case, a position of the ejection port 51a is configured to be fixed in a state in which the ejection port 51a of the water supply tube 51 is at the proximal end of the slit 17.

Next, an operation of the cleaning mechanism 50 will be mainly described with respect to an operation of the medical device 1B of this embodiment. The cleaning mechanism 50 can be used as a water supply port for supplying cleaning water to a treatment target portion in a state (see FIG. 13) in which the treatment portion 3 is positioned outside the storage portion 18. At this time, it is possible to dispose the ejection port 51a at a position near the treatment target portion by moving the position of the ejection port 51a of the water supply tube 51 to the distal end of the slit 17 or further from the slit 17 to the distal end using the position change mechanism 52. In addition, the cleaning mechanism 50 also has a function of cleaning the treatment portion 3 by supplying the cleaning water to the treatment portion 3 in a state in which the treatment portion 3 is positioned outside the storage portion 18.

In this embodiment, the case (see FIG. 15) in which the treatment portion 3 outside the storage portion 18 is accommodated in the storage portion 18 will be described. First, the position change mechanism 52 moves a position of the ejection port 51a of the distal end of the water supply tube 51 to the proximal end of the slit 17. Thereby, the slit 17 is open and an entrance for introducing the treatment portion 3 into the storage portion 18 is generated. When the position change mechanism 52 is not provided, the slit 17 is constantly in an open state and the treatment portion 3 can pass through the slit 17.

Subsequently, in a process in which the treatment tool rotates around the center of rotation of the rotating shaft 11 until the treatment portion 3 passes through the slit 17, the cleaning water is ejected from the ejection port 51a of the distal end of the water supply tube 51. Thereby, the treatment portion 3 moves from the outside of the storage portion 18 to the inside of the storage portion 18, so that the cleaning water contacts the treatment portion 3 and a foreign substance attached to the treatment portion 3 is removed.

Once the treatment portion 3 enters the storage portion 18, the supply of the cleaning water may start. In this case, when the treatment portion 3 is accommodated within the storage portion 18, a foreign substance is removed inside of the storage portion 18.

In addition, in this embodiment, certainty that the cleaning water output from the ejection port 51a reaches a hook portion 5 is high because the hook portion 5 of the distal end of the treatment portion 3 is rotated to be close to the ejection port 51a. A frequency at which the distal end of the treatment portion 3 is in contact with the treatment target portion when the treatment is performed on the treatment target portion is high and the distal end of the treatment portion 3 is a part to which the foreign substance is easily attached. In particular, a foreign substance such as burnt tissue is easily attached to the hook portion 5 in the hook type incision electrode 4 for performing the incision using a high-frequency current. In the medical device 1B of this embodiment, it is possible to efficiently clean the distal end of the treatment portion 3.

Modified Example

Next, the modified example of this embodiment will be described with reference to FIG. 16.

FIG. 16 is a schematic perspective view showing a configuration of the modified example of the medical device.

As shown in FIG. 16, the medical device in this modified example has a different configuration from the above-described medical device 1B in that there is provided a means for scraping off a foreign substance attached to the distal end of the treatment portion 3. That is, the medical device 1C of this modified example includes a brush 50A (cleaning mechanism 50A) attached to a slit 17 of a support portion 12 instead of the cleaning mechanism 50.

The brush 50A, for example, has stiffness to a degree at which it is possible to scrape off a fragment of living tissue fixed to the hook portion 5 of the incision electrode 4.

In addition, the cleaning mechanism 50A may have a spatula having flexibility according to a resin such as a rubber and having stiffness to a degree at which it is possible to scrap off a foreign substance in the slit 17 instead of the brush 50A.

Fourth Embodiment

Next, an embodiment of a medical system of the present invention will be described with reference to FIGS. 17 to 20. In this embodiment, the configuration and operation of the medical device provided in a medical system of this embodiment are similar to those of the medical device 1 of the first embodiment except for particularly specified matter.

Figure 17:
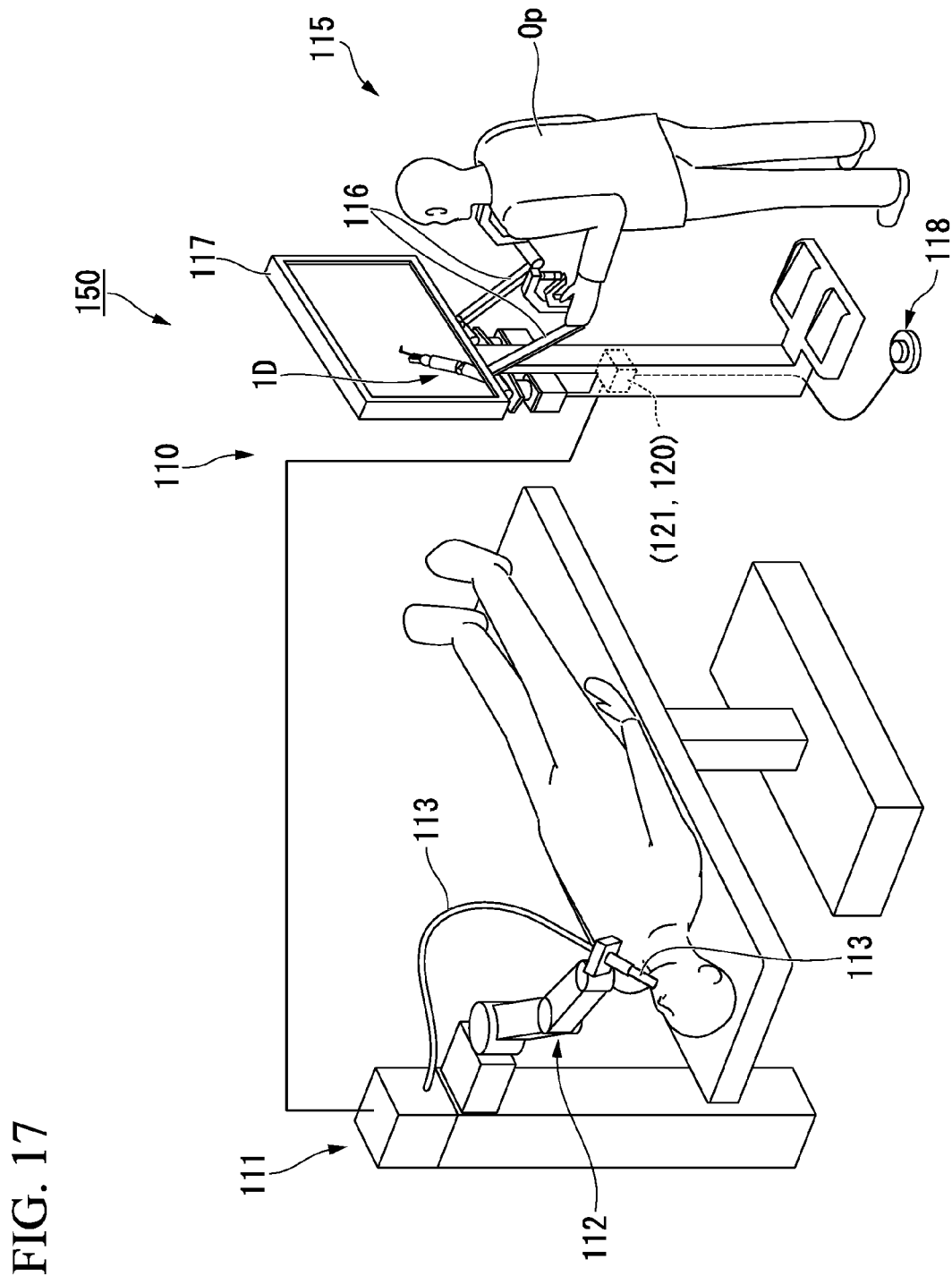
FIG. 17 is a schematic entire view of a medical system of a fourth embodiment of the present invention.
Figure 18:
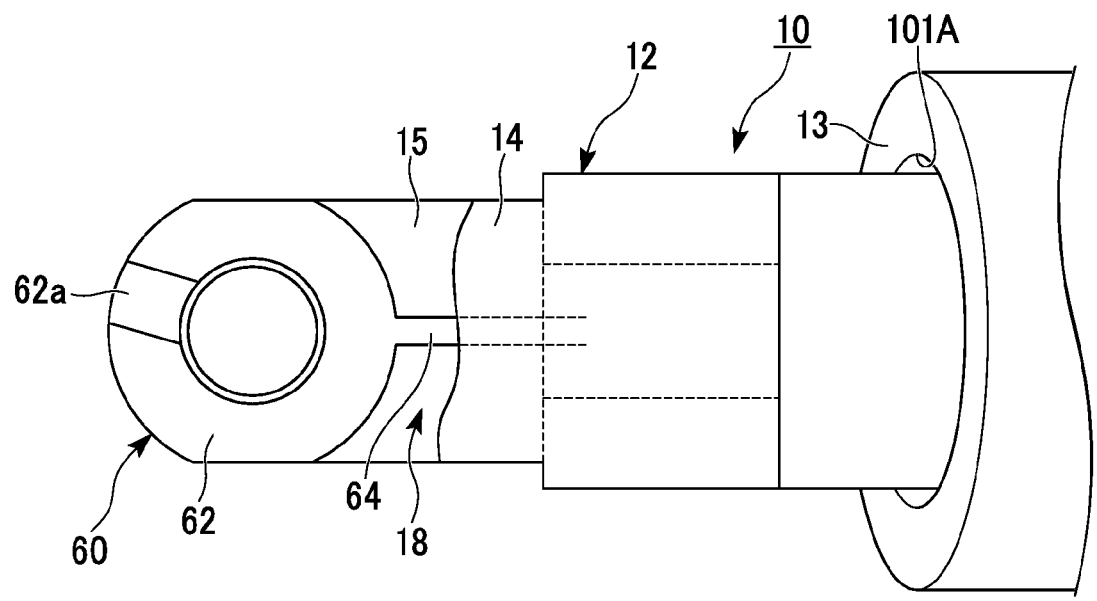
FIG. 18 is a schematic view showing a partially discontinuous distal end part of the medical device of the fourth embodiment provided in the medical system.
Figure 19:
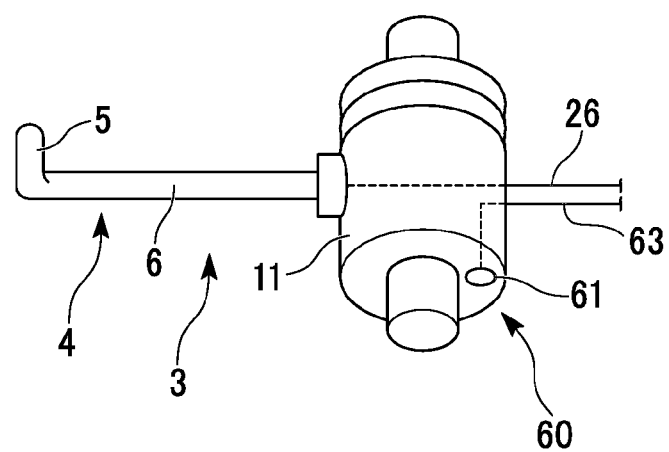
FIG. 19 is a schematic perspective view showing a configuration of a switch portion provided in a joint portion after part of the joint portion of the medical device is enlarged.
Figure 20:
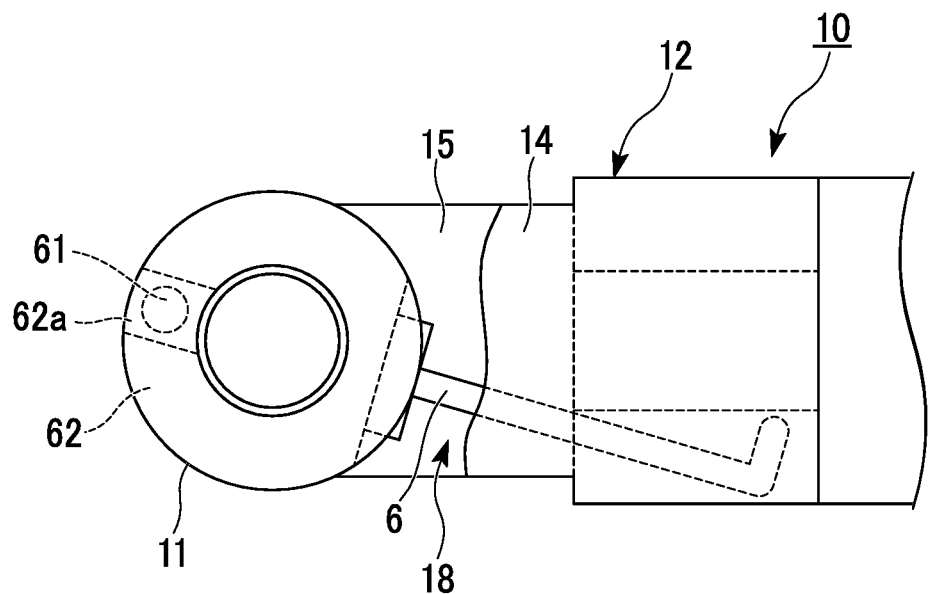
FIG. 20 is a schematic view showing an operation of the medical device.
Figure 23:
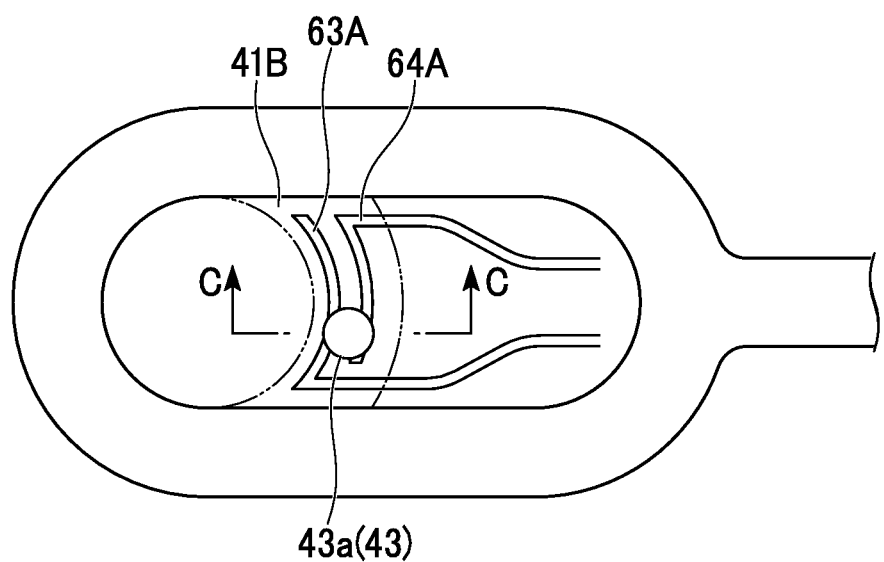
FIG. 23 is an explanatory view showing an operation of the modified example.
Figure 24:
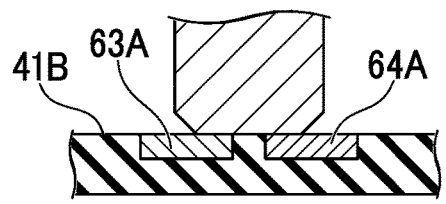
FIG. 24 is a cross-sectional view taken along line C-C of FIG. 23.

FIG. 17 is a schematic entire view of the medical system of a fourth embodiment of the present invention. FIG. 18 is a schematic view showing a partially discontinuous distal end part of the medical device of the fourth embodiment provided in the medical system. FIG. 19 is a schematic perspective view showing a configuration of a switch portion provided in a joint portion after part of the joint portion of the medical device is enlarged. FIG. 20 is a schematic view showing an operation of the medical device. FIG. 24 is a cross-sectional view taken along line C-C of FIG. 23.

As shown in FIG. 17, the medical system 150 includes a medical manipulator device 110 for allowing an operator who operates on a patient to perform the surgical manipulation on the patient and a medical device 1D attached to the medical manipulator device 110.

The medical manipulator device 110 includes a slave medical manipulator 111 to which the medical device 1D is attached, a master medical manipulator 115 electrically connected to the slave medical manipulator 111 and configured to issue an operation command to the slave medical manipulator 111, and a control unit 120 configured to control the entire medical system 150.

The slave medical manipulator 111 includes a slave arm 112 to which at least the above-described medical device 1D is attached, an actuator (not shown) configured to operate the slave arm 112, and a sensor (not shown) for detecting the position of the slave arm 112.

The slave medical manipulator 111 receives an operation command from the master medical manipulator 115 and operates the slave arm 112 and the medical device 1D according to the operation command. That is, in this embodiment, the slave medical manipulator 111 can be connected to at least a driving force generation portion 32 of the medical device 1D and operate the driving force generation portion 32 in correspondence with the operation command from the master medical manipulator 115.

The slave arm 112 of this embodiment has a flexible long shaft member 113 to be inserted into a body and a channel 101A for passing the insertion portion 2 of the medical device 1D within the long shaft member 113. An imaging mechanism (not shown) for observing the treatment target portion is provided at the distal end of the long shaft member 113 of the slave arm 112. This imaging mechanism acquires an image of the treatment target portion.

The master medical manipulator 115 has a master arm 116 and a display unit 117. The master arm 116 is used for allowing an operator Op to operate the medical device 1D by holding and moving the master arm 116 manually. The display unit 117 is used for displaying an image acquired by the imaging mechanism provided in the long shaft member 113 of the slave arm 112. Further, the master medical manipulator 115 in this embodiment includes a storage state control switch 118. The storage state control switch 118 is configured to transmit a trigger signal, used for accommodating the treatment portion 3 in the medical device 1D in the storage portion 18 and sending out the treatment portion 3 from the storage portion 18, to the control unit 120.

In the master medical manipulator 115, the master arm 116 is operated and therefore the operation command is issued to the control unit 120.

The control unit 120 outputs a signal for operating the slave medical manipulator 111 to the slave medical manipulator 111 based on the operation command and the trigger signal transmitted from the master medical manipulator 115.

The control unit 120 outputs a signal for operating the driving force generation portion 32 of the medical device 1D. In addition, the control unit 120 includes a determination unit 121 configured to determine a state in which the treatment portion 3 is inside the storage portion 18 and a state in which the treatment portion 3 is outside the storage portion 18.

As shown in FIG. 18, the medical device 1D is different from the medical device 1 described in the first embodiment in that a switch portion 60 is provided in a joint portion 10. It is possible to distinguish between the state in which the treatment portion 3 is inside the storage portion 18 and the state in which the treatment portion 3 is outside the storage portion 18 according by the conductive state of the switch portion 60.

Further, the driving force generation portion 32 of the medical device 1D is connected to the control unit 120 of the medical manipulation device 110. Thereby, the driving force generation portion 32 of the medical device 1D is configured to perform traction motion on a first wire 24 and a second wire 25 in correspondence with the operation command based on an operation input from the master arm 116 and the trigger signal transmitted from the storage state control switch 118 of the master medical manipulator 115.

As shown in FIGS. 18 and 19, the switch portion 60 includes a first contact point 61, a second contact point 62, a first wiring 63, and a second wiring 64. The first contact point 61 is fixed to the rotating shaft 11 of the joint portion 10. The second contact point 62 has two states of a contact state and a separation state with respect to the first contact point 61 fixed to the support portion 12. The first wiring 63 is configured to electrically connect the first contact point 61 and the determination unit 121. The second wiring 64 is configured to electrically connect the second contact point 62 and the determination unit 121.

As shown in FIG. 19, the first contact point 61 is disposed in part of a circle centering on the center of rotation of the rotating shaft 11 in any one end surface in a center of rotation direction of the rotating shaft 11.

As shown in FIG. 18, the second contact point 62 is disposed in one (the second wall portion 15 in this embodiment) of a first wall portion 14 and a second wall portion 15 of the support portion 12 close to the first contact point 61.

In addition, the second contact point 62 has an arc shape along part of a circle having approximately the same radius as the above-described circle centering on the center of rotation of the rotating shaft 11. The arc shape of the second contact point 62 is a C shape having a break 62*a* in at least a part thereof.

The break 62*a* in the arc shape of the second contact point 62 has a width of an extent to which the first contact point 61 can enter the break 62*a* without contact with the second contact point 62. The break 62*a* is positioned so that the first contact point 61 enters the break 62*a* and the first contact point 61 and the second contact point 62 are in a non-contact state in a state in which the treatment portion 3 is disposed within the storage portion 18.

Next, details of configurations of the determination unit 121 and the control unit 120 in the medical system 150 of this embodiment will be described with an operation of the medical system 150.

In this embodiment, the storage state control switch 118 of the master medical manipulator 115 is pushed by the operator and therefore the loading/unloading of the treatment portion 3 with respect to the storage portion 18 starts based on a trigger signal.

The determination unit 121 distinguishes and determines a first state and a second state by detecting whether the first contact point 61 and the second contact point 62 of the switch portion 60 are conductive. In the first state, the first contact point 61 and the second contact point 62 are conductive. That is, in the first state, the treatment portion 3 is outside the storage portion 18 (see FIG. 18). In the second state, the first contact point 61 and the second contact point 62 are not conductive. That is, in the second state, the treatment portion 3 is inside the storage portion 18 (see FIG. 20).

When the first contact point 61 and the second contact point 62 are conductive, the determination unit 121 returns information indicating that the treatment portion 3 has exited the storage portion 18 and the treatment on the treatment target portion is possible to the control unit 120. On the other hand, when the first contact point 61 and the second contact point 62 are not conductive, the determination unit 121 returns information indicating that the treatment portion 3 is accommodated inside the storage portion 18 and the treatment on the treatment target portion is impossible to the control unit 120.

When the first contact point 61 and the second contact point 62 are not conductive, the determination unit 121 may be configured to return information indicating that the treatment portion 3 is accommodated inside the storage portion 18 and that the medical device 1D can be replaced to the control unit 120.

The control unit 120 causes the display unit 117 to display a status in which an operation using the master arm 116 of the master medical manipulator 115 can be input when the treatment is possible based on a determination result of the determination unit 121. Further, the control unit 120 transmits the motion of the master arm 116 of the master medical manipulator 115 as an operation command for the slave medical manipulator 111 to the slave medical manipulator 111.

On the other hand, when the treatment is not possible, the control unit 120 causes the display unit 117 to display that an operation input using the master arm 116 of the master medical manipulator 115 is impossible and invalidates the operation command based on the motion of the master arm 116 of the master medical manipulator 115. In addition, when the medical device 1D can be replaced, the control unit 120 causes the display unit 117 to display a status in which the medical device 1D can be replaced and invalidates the operation command based on the motion of the master arm 116 of the master medical manipulator 115.

The operator of the medical system 150, for example, can manually replace the medical device 1D with the medical device 1 which is similar to the medical device 1D of this embodiment but has a different configuration in terms of the treatment portion 3 or a reserve medical device 1D of this embodiment.

That is, in this embodiment, the medical system 150 is configured to perform switching between a treatment mode in which the treatment using the treatment portion 3 is possible and a device replacement mode in which the replacement of the medical device 1 is possible.

The medical device 1D newly inserted into the channel 101A of the long shaft member 113 is in a state in which the treatment portion 3 is accommodated in the storage portion 18. Once the medical device 1D newly inserted into the channel 101A is reliably inserted into the channel 101A, the operator presses the storage state control switch 118. Thereby, the treatment portion 3 of the medical device 1D is delivered from the storage portion 18 through the slit 17 and is in a state in which the treatment is possible.

According to the medical system 150 of this embodiment, it is possible to reliably find that the treatment portion 3 is accommodated in the storage portion 18 without depending on an image obtained by imaging the treatment target portion because the determination unit 121 determines whether the treatment portion 3 is in an accommodated state in the storage portion 18 in the control unit 120.

In addition, the loading/unloading of the treatment portion 3 for the storage portion 18 can be performed according to the use of the master medical manipulator 115.

Modified Example

Next, the modified example of this embodiment will be described with reference to FIGS. 21 to 24.

Figure 21:
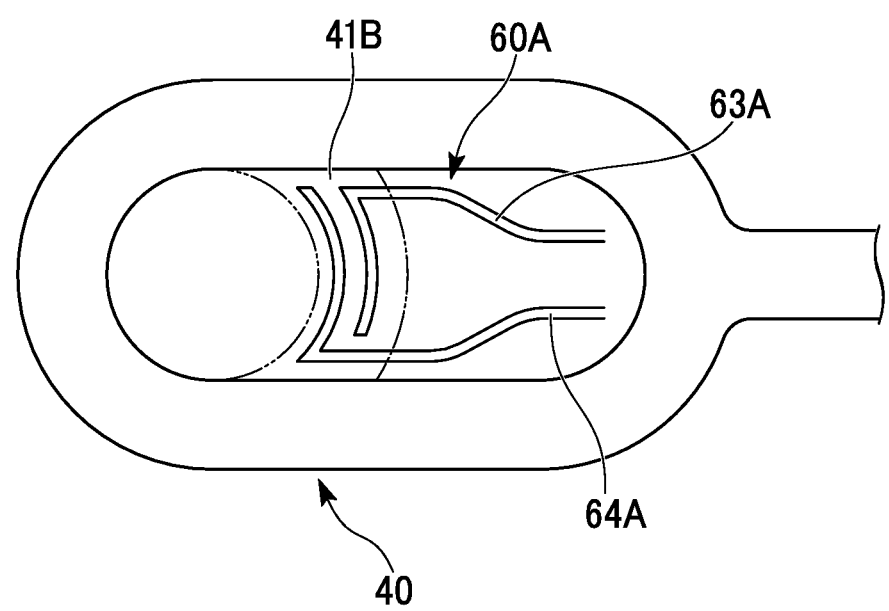
FIG. 21 is a schematic view showing a configuration of a modified example of the medical device.
Figure 22:
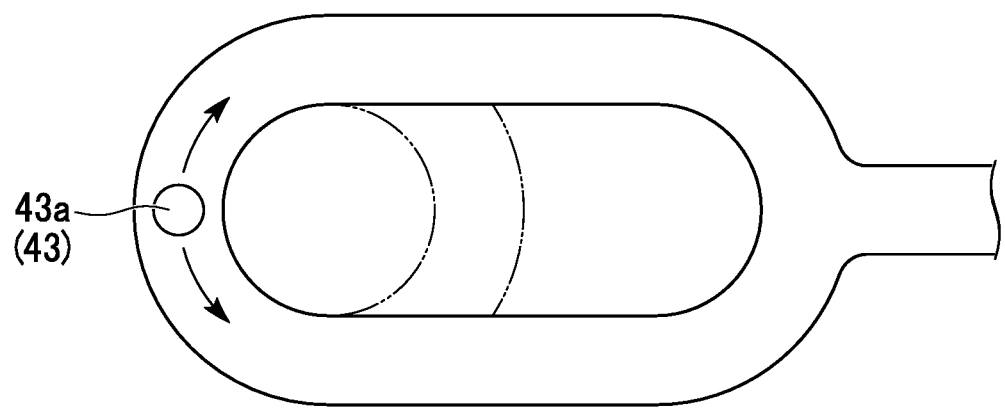
FIG. 22 is an explanatory view showing an operation of the modified example.

FIG. 21 is a schematic view showing a configuration of the modified example of the medical device. FIG. 22 is an explanatory view showing an operation of the modified example. FIG. 23 is an explanatory view showing an operation of the modified example.

As shown in FIG. 21, in this modified example, a switch portion 60A having a different configuration from the above-described switch portion 60 is provided for the medical device 1A described in the second embodiment.

That is, in this modified example, the switch portion 60A for causing the determination unit 121 to determine the storage state of the treatment portion 3 for the storage portion 18 is provided in a part of the switching mechanism 40 described in the second embodiment.

The switch portion 60A has a first wiring 63A and a second wiring 64A having distal ends disposed in an insulation region 41B. A protruding end portion 43a of a columnar terminal 43 is in contact with both the distal end of the first wiring 63A and the distal end of the second wiring 64A and therefore a current is applied (see FIGS. 23 and 24).

In addition, in a state in which the columnar terminal 43 is conductive with only the spring terminal 42, the first wiring 63A and the second wiring 64A are in an insulated state and a high-frequency current can be applied to the columnar terminal 43 through the spring terminal 42. A proximal end of the first wiring 63A and a proximal end of the second wiring 64A are connected to the determination unit 121. Thus, it is possible to determine the storage state of the treatment portion 3 by determining whether the first wiring 63A and the second wiring 64A is in the conductive state through the columnar terminal 43.

Even in this modified example, similar effects to this embodiment are obtained.

Modified Example

Next, another modified example of this embodiment will be described.

In this modified example, the determination unit 121 determines whether the treatment portion 3 is inside the storage portion 18 by referring to an amount of traction of the first wire 24 by a first actuator 33.

Even in this configuration, similar effects to this embodiment are obtained.

Modified Example

Next, still another modified example of this embodiment will be described.

In this modified example, some examples in which the control unit 120 controls other parts of the medical device 1D are shown.

When the treatment portion 3 is accommodated in the storage portion 18, the control unit 120 may control the application of a high-frequency current to the incision electrode 4 to be inhibited. That is, in this modified example, the applied current control of the high-frequency current for the incision electrode 4 is performed by the control unit 120. In the case of this modified example, it is unnecessary to provide the switching mechanism 40 of the conductive state of the high-frequency current as described in the second embodiment.

In addition, when the treatment portion 3 is accommodated in the storage portion 18, the control unit 120 may control the long shaft member 113 of the slave arm 112 to be relaxed. In this case, the long shaft member 113 of the slave arm 112 can be freely curved through an operation of the master arm 116 of the master medical manipulator 115. Because the above-described relaxing control by the control unit 120 is interposed in curving motion of the long shaft member 113 of the slave arm 112, it is possible to relax the long shaft member 113 of the slave arm 112 in the purpose for easily replacing the medical device 1D when the treatment portion 3 is accommodated in the storage portion 18. When a joint other than the joint portion 10 is provided in the medical device 1D, the control unit 120 can also easily replace the medical device 1D by setting the other joint in a relaxed state.

While preferred embodiments of the invention have been described and illustrated above, the invention is not limited to these. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical device comprising:
an insertion portion which is capable of being inserted into a body; and
a driving mechanism which is coupled to the insertion portion,
wherein the insertion portion includes:
   a treatment portion which is configured to perform a treatment on a treatment target portion;
   a joint portion which is configured to be capable of supporting the treatment portion and changing a direction of the treatment portion;
   a storage portion which is configured in the joint portion and capable of internally accommodating the treatment portion; and
   a driving force transmission portion which is connected to the joint portion and configured to transmit a driving force for changing the direction of the treatment portion to the joint portion,
wherein the driving mechanism includes a driving force generation portion which is configured to generate the driving force connected to the driving force transmission portion,
wherein the treatment portion enters and exits the storage portion by the driving force transmitted from the driving force generation portion to the joint portion through the driving force transmission portion,
wherein the treatment portion includes an incision electrode which is configured to receive a supply of a high-frequency current to incise living tissue,
wherein the joint portion includes a switching mechanism which is configured to switch a conductive state of the high-frequency current for the incision electrode,
wherein the insertion portion includes a power supplying cable which is connected to the switching mechanism and from which the high-frequency current is applied,
wherein the driving mechanism includes a plug which is connected to the power supplying cable and connectable to a high-frequency power supply device, and
wherein the switching mechanism cuts off a current applied to the power supplying cable and the incision electrode when the incision electrode is positioned inside the storage portion, and electrically connects the power supplying cable and the incision electrode when the incision electrode is positioned outside the storage portion.

2. The medical device according to claim 1, further comprising:
a cleaning mechanism in which the treatment portion removes a foreign substance attached to the treatment portion in a process of movement from an outside of the storage portion to an inside of the storage portion or within the storage portion.

3. A medical system comprising:
the medical device according claim 1;
a master medical manipulator configured to receive an operation input from an operator;
a control unit connected to the master medical manipulator;
a slave medical manipulator connected to the control unit and connected to the driving mechanism; and a determination unit provided in the control unit and configured to determine a state in which the treatment portion is inside the storage portion and a state in which the treatment portion is outside the storage portion.

* * * * *